United States Patent [19]

Yonsel et al.

[11] Patent Number: 5,312,980
[45] Date of Patent: May 17, 1994

[54] PROCESS FOR THE SEPARATION OF AMINO ACIDS FROM AQUEOUS SOLUTIONS

[75] Inventors: Sems Yonsel, Hanau; Wiltrud Schäfer-Treffenfeldt, Obertshausen; Akos Kiss, Hanau; Elfriede Sextl, Geiselbach; Heike Kinz, Hanau, all of Fed. Rep. of Germany

[73] Assignee: Degussa Aktiengesellschaft, Fed. Rep. of Germany

[21] Appl. No.: 55,313

[22] Filed: May 3, 1993

[30] Foreign Application Priority Data

May 23, 1992 [DE] Fed. Rep. of Germany ....... 4217203

[51] Int. Cl.⁵ .................. C07C 227/40; C07C 229/26; C07C 229/22
[52] U.S. Cl. .................................................... 562/554
[58] Field of Search ............................................ 562/554

[56] References Cited

U.S. PATENT DOCUMENTS

| | | | |
|---|---|---|---|
| 3,630,681 | 12/1971 | Arikawa | 562/553 X |
| 4,687,871 | 8/1987 | Comyns et al. | 564/424 X |
| 4,691,054 | 9/1987 | Tosa et al. | 562/554 |
| 4,837,371 | 6/1989 | Ogawa et al. | 562/554 X |
| 4,842,935 | 6/1989 | Shinbo et al. | 428/404 |
| 4,910,336 | 3/1990 | Goodman | 562/443 |
| 4,923,616 | 5/1990 | Hirata et al. | 210/676 |
| 5,104,492 | 4/1992 | King et al. | 562/554 X |

FOREIGN PATENT DOCUMENTS 750402 5/1943 Fed. Rep. of Germany .

Primary Examiner—Arthur C. Prescott
Attorney, Agent, or Firm—Cushman, Darby & Cushman

[57] ABSTRACT

A process for the separation of amino acids from aqueous solutions by adsorption on zeolites of different types. It is unnecessary to separate the biomass prior to the treatment.

8 Claims, 5 Drawing Sheets

PROCESS FOR THE SEPARATION OF AMINO ACIDS FROM AQUEOUS SOLUTIONS

The present invention relates to a process for the separation of amino acids from aqueous solutions.

BACKGROUND OF THE INVENTION

Individual amino acids are produced commercially in four ways:
(a) Separation of the amino acids from naturally occurring and renewable raw materials (e.g. chicken feathers, pig bristles);
(b) Chemical synthesis (e.g. DL-methionine);
(c) Enzymatic production from chemical precursors (e.g. L-methionine);
(d) Microbiological production, fermentation (e.g. L-lysine, L-threonine, L-tryptophan).

In all these processes and methods the separation and isolation of the amino acids is one of the essential process steps.

For this purpose organic ion-exchange resins are frequently used.

L-lysine is e.g. adsorbed on strongly acidic ion exchanger resins of the $NH_4^+$ type, at a pH value of 0.5 to 3, the loaded exchanger is then eluted with ammonia water and the desired L-lysine hydrochloride formed by addition of hydrochloric acid (see U.S. Pat. No. 3,565,951).

SUMMARY OF THE INVENTION

It is the object of the invention to provide a further way of separating that also enables L-lysine hydrochloride or sulfate to be obtained directly.

The present invention provides a process for the separation of amino acids from aqueous solutions in which these solutions are passed over zeolites and the adsorbed amino acid(s) subsequently are isolated by desorption from the zeolites.

The solutions used in carrying out the method of the invention originate in particular from fermentation processes for the production of amino acids or are obtained in processes in which solutions containing amino acids are produced by the hydrolysis of natural products, such as e.g. chicken feathers or pig bristles.

Adsorption and desorption are carried out at temperatures between 5° and 100° C., in particular 15° to 40° C. The kinetics of these steps are influenced to only a small degree by the temperature.

In general the concentration of amino acids in the solutions ranges up to the solubility limit, in particular 0.1 to 15 wt %. =5.7), and acidic amino acids are preferably adsorbed at The adsorption, like the desorption, is pH-dependent. In this connection, it has been observed that basic amino acids, such as e.g. L-lysine (pI=9.6), are preferably adsorbed at the isoelectric point and in the basic range (pH≧pI), while neutral amino acids, e.g. L-methionine and L-threonine (pI=5.7), and acidic amino acids are preferably adsorbed at the isoelectric point and in the acid range (pH≦pI). The desorption occurs at the corresponding opposite pH values, pH<pI or pH>pI.

The pH which is observed when an amino acid is dissolved in deionized water also approximately corresponds to the isoelectric point pI of this amino acid.

The solutions to be treated are therefore preferably adjusted, by addition of acids or alkaline substances, to the pH ranges in which adsorption and desorption is preferably carried out, as is generally known.

The same applies if the pH value of the solution shifts during the adsorption.

Obviously the amino acids must be stable at the pH values adjusted in each case for the adsorption or desorption.

The zeolites can be used in powder form or also molded, e.g. in a fixed bed. There are then preferably usable as molding aids, as is generally known, e.g. alkyl silicates or their hydrolyzates or bentonites.

For the adsorption of amino acids in aqueous solutions, zeolites with various pore sizes, structures, degrees of dealumination and cations are used. The following table indicates a selection of the zeolites that are usable for the purpose of the invention, with their properties.

TABLE 1

Zeolite types for adsorption in solutions

| Zeolite | Modulus $SiO_2/Al_2O_3$ | Pore width [Å] | Reference |
|---|---|---|---|
| Zeolite A | ca. 2 | 3–5 | (1, 2) |
| Zeolite X | ca. 2–3 | ca. 7.4 | (1) |
| Zeolite Y, dealuminized zeolite Y (DAY) | 3–∞ | ca. 7.4 | (1, 3, 4) |
| Mordenite, dealuminized mordenite | ≧10 | 6.5 × 7 | (1, 5) |
| ZSM-5, dealuminized ZSM-5 | 20–∞ | 5 3 × 5.6<br>5.1 × 5.5 | (5, 6) |
| Zeolite β | 20–∞ | 7.5 × 5.7<br>6.5 × 5.6 | (7) |
| VIP-5 | — | 12.1 | (8) |

References
(1) D.W. Breck, Zeolite Molecular Sieves, Structure, Chemistry and Use, J. Wiley & Sons, New York 1974;
(2) H. Strack et al., (Degussa A.G.), DE 2660722 C2;
(3) E. Roland et al., (Degussa A.G.), EP 0413138;
(4) H.K. Beyer, I. Belenykaja, Catalysis by Zeolites, Elsevier, Amsterdam 1980;
(5) C.D. Chang, (Mobil Oil Corp.) US-PS 4,273,753;
(6) F.G. Dwyer et al., (Mobil Oil Corp.), DE 2836076 C2;
(7) R.B. Calvert et al., (Mobil Oil Corp.), EP 0164208;
(8) W. Schmidt et al., Zeolites 12 (1992), Jan., 2ff.

It becomes evident that the loading of the various zeolite types depends on the amino acid concentration in the solution and on the amino acid itself.

It follows that for the separation of each amino acid there are particularly suitable zeolites. They can easily be identified by recording the adsorption isotherms. Thus at a pH value of 9 to 10 with L-lysine on DAY, a maximum measured loading of about 12 to 13% is reached; on ZSM-5 or mordenite, ca. 8%; and on NaY, 10%.

For L- and DL-methionine the best loading results are found on ZSM-5, i.e., about 9%, at pH 1 to 6. On DAY, the loading limit is not reached in the concentration range investigated; on mordenite the maximum loading is 4%.

On DAY and ZSM, L-threonine reaches the following loadings: 5% on ZSM05, .4% on mordenite and 1% on DAY. The trend of the adsorbability on the same zeolites is similar in the case of L-threonine to that in the case of L-/DL- methionine: both are weakly acidic amino acids, and the loadings on ZSM-5 and DAY are less.

With the aid of the process according to the invention it is not only possible, however, to remove amino acids from aqueous solutions.

It is also possible to separate amino acid mixtures.

From a solution containing L-lysine, L-methionine and L-threonine, with the aid of ZSM-5, L-methionine can be separated by adsorption in the acid pH range (pH=ca. 1). When working the alkaline pH range (pH=ca. 9), L-lysine is selectively adsorbed from this mixture.

Under these conditions, L-lysine can also be separated by using zeolites of the mordenite or DAY or NaY type.

The amino acids adsorbed on the particular zeolites used are desorbed at pH values that for neutral amino acids (e.g. methionine, threonine) are preferably above and for basic amino acids (e.g. lysine) preferably below the pI value.

In this way it is possible to obtain e.g. lysine hydrochloride or sulfate directly.

The recovery rate of the adsorbed L-lysine reaches 100% at a pH of ca. 1 on DAY and NaY. Sulfuric acid or hydrochloric acid is preferably used as the acid for the desorption step. DL- and L-methionine are completely desorbed at a pH value of ca. 10.

The process can be carried out continuously or discontinuously, according to the requirements, for example by passing a sidestream from a fermentation continuously through a zeolite bed and after separation of the desired amino acid returning the sidestream to the fermentation vessel.

FIG. 5 shows a diagram of the process. A base, e.g., ammonia, is added to the reactor during the fermentation as a pH correcting agent. For the in situ workup, fermentation broth is withdrawn from the reactor in the by-pass via a sterile pump and the broth is recycled back to the reactor by pumping via a column with the zeolite packing. No separation of cells occurs. L-lysine is adsorbed on the zeolite packing, while low-lysine broth is recycled by pumping to the reactor.

The pumping rate or, to be more exact, the residence time in the by-pass and column, must be so chosen that the cells suffer no damage because of a shortage of oxygen and substrate.

If necessary, different adsorption stages are also connected in series, which optionally also are operated under different conditions (pH value, zeolite type), if, e.g., it is intended to separate various amino acids from each other. Altogether a number of advantages arise when, contrary to the use of organic ion exchanger resins known from the prior art, zeolites are used for the adsorption of amino acids.

TABLE 2

Comparison of the methods of working-up: Adsorption on zeolites and ion exchangers

| Adsorption | |
|---|---|
| on zeolites | on ion-exchanger resins |
| no regenerating; desorption is at the same time a regeneration step as a result, lower salinity in the waste water | the resin must be regenerated before loading with acid |
| elution with various acids (e.g. for the production of various lysine salts during the desorption) | after the elution the solution must be converted with the corresponding acid to the desired salts |
| no swelling of the-adsorbent | the swelling of the resin causes problems: blocking up, loss of capacity |
| mechanical strength is high; also fragments of the molded bodies achieve maximum loadings elevated temperatures do not reduce the adsorption capacity; high temperature stability | broken resin spheres lose their loading properties |
| proteins, biomass, dissolved salts do not interfere with the adsorption properties | proteins influence the loading negatively and must be separated beforehand; foreign ions interfere with the loading |

BRIEF DESCRIPTION OF FIGURES OF DRAWING

The invention will be further described by reference to the drawings, in which.

DETAILED DESCRIPTION OF PREFERRED EMBODIMENTS

The following examples illustrate the practice of the invention.

Examples

1. Working-up of amino acid solutions

The experiments on adsorption of amino acids on zeolites were carried out statically in stirred or shaken 100 ml flasks.

Synthetic amino acid solutions of various concentrations (Concentrations $C_0$ up to 80 g/l were used).

The following types of zeolite were used as adsorbents:

TABLE 3

| | $SiO_2/Al_2O_3$ | Si/Al | Micropore volume (ml/g) | Calcination (°C.) | (h) |
|---|---|---|---|---|---|
| NaY | 6 | 3 | 0.3 | none | |
| H-mordenite | 20 | 10 | 0.2 | 550 | 1 |
| H-ZSM-5 | 45 | 23 | 0.2 | 550 | 1 |
| DAY | 200 | 100 | 0.3 | 950 | 1 |

In each case, 3 g of the powdery zeolite, saturated with atmospheric moisture, were weighed and added, e.g., to a flask with 30 ml L-lysine solution. The experiments ran overnight (16 to 20 h). The samples were filtered and the zeolite-free supernatant liquid analyzed by means of an HPLC system.

The adsorption experiments were carried out at room temperature and at 35° C. and 60° C. The quantities adsorbed were found by analysis of the lysine concentration at the start ($C_0$) and at the end ($C_f$) of the experiment. The remaining difference is adsorbed. With the knowledge of the adsorbent concentration ($C_z$=g zeolite/g amino acid in the solution), the loading X can be determined:

$$[X=] \frac{[C_0][C_i]}{C_z} \, [\%]$$

Figure 1:
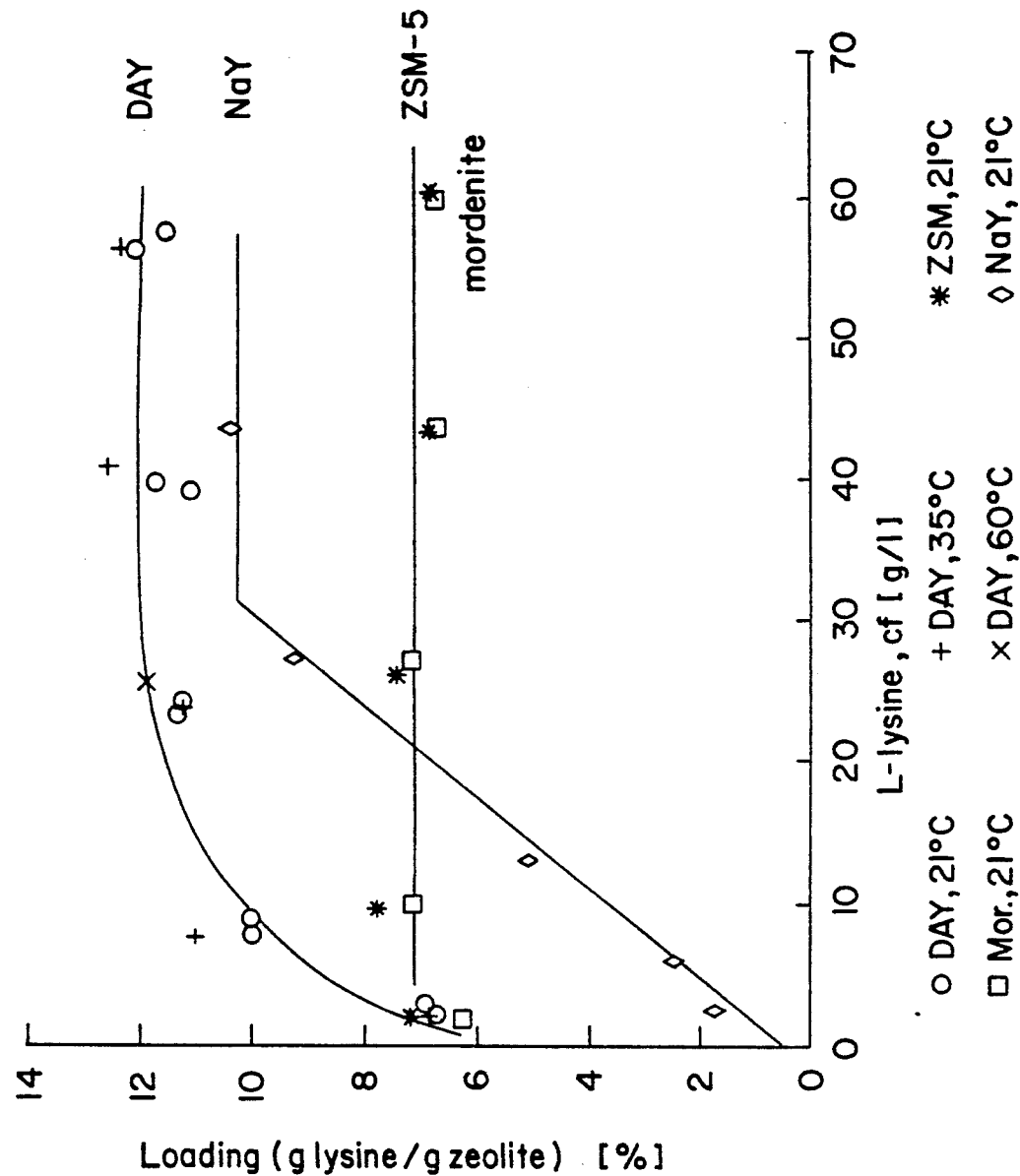
FIG. 1 is a plot of adsorption isotherms of L-lysine on DAY, ZSM-5, mordenite and NaY powders.

FIG. 1 shows the adsorption isotherms of L-lysine monohydrate. The solutions used had, together with zeolite, an average pH value of 9.5.

Between H-ZSM-5 and H-mordenite no differences are detectable. On both zeolites a maximum loading of about 8% is reached.

The loading of DAY under the same conditions (T=21° C.) reaches a maximum of about 13%. Experiments at 35° C. and 60° C. show that temperature increases have no effect on the adsorption.

Figure 2:
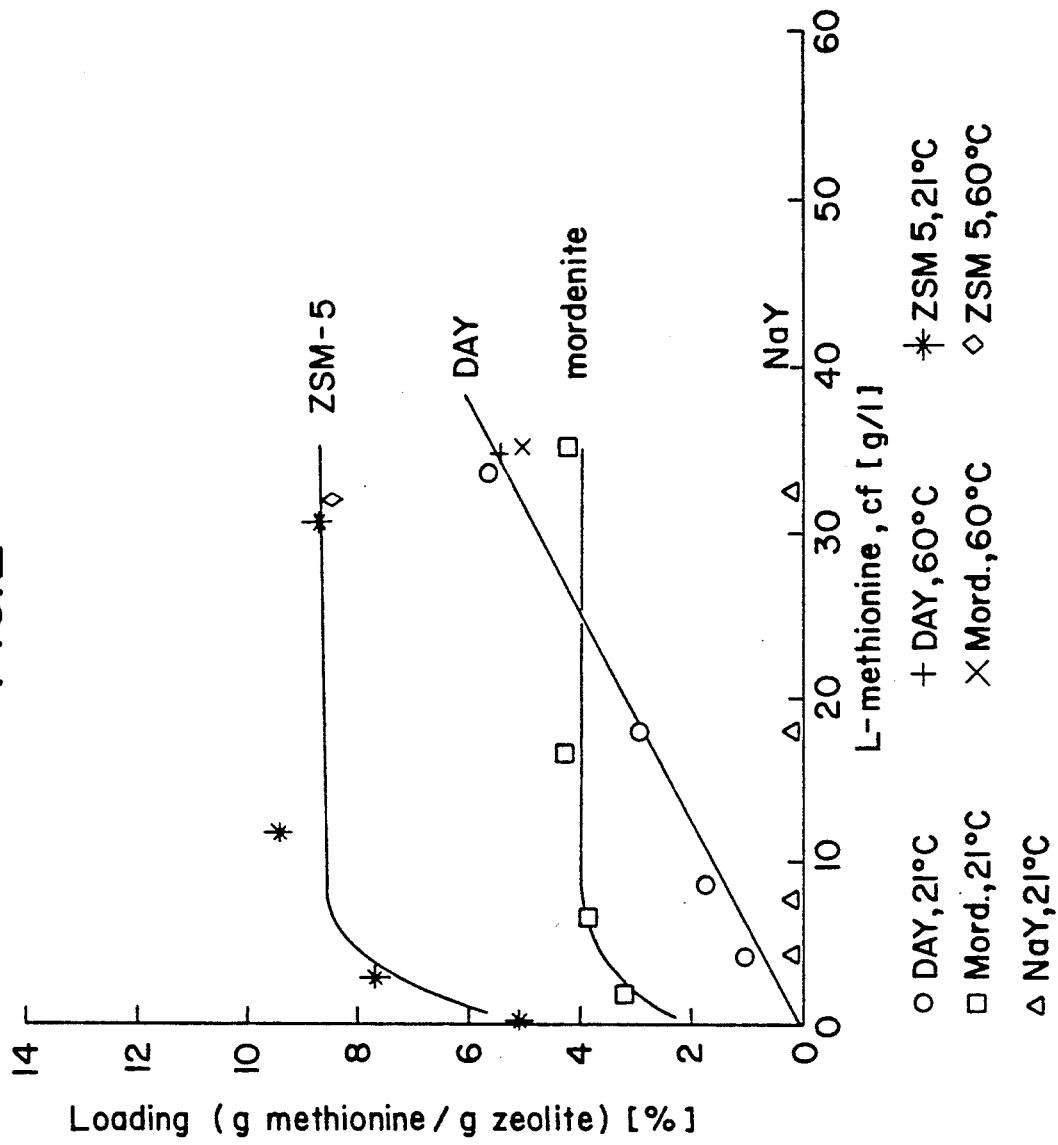
FIG. 2 is a plot of adsorption isotherms of L-methionine on DAY, ZSM-5, mordenite and NaY powders.
Figure 3:
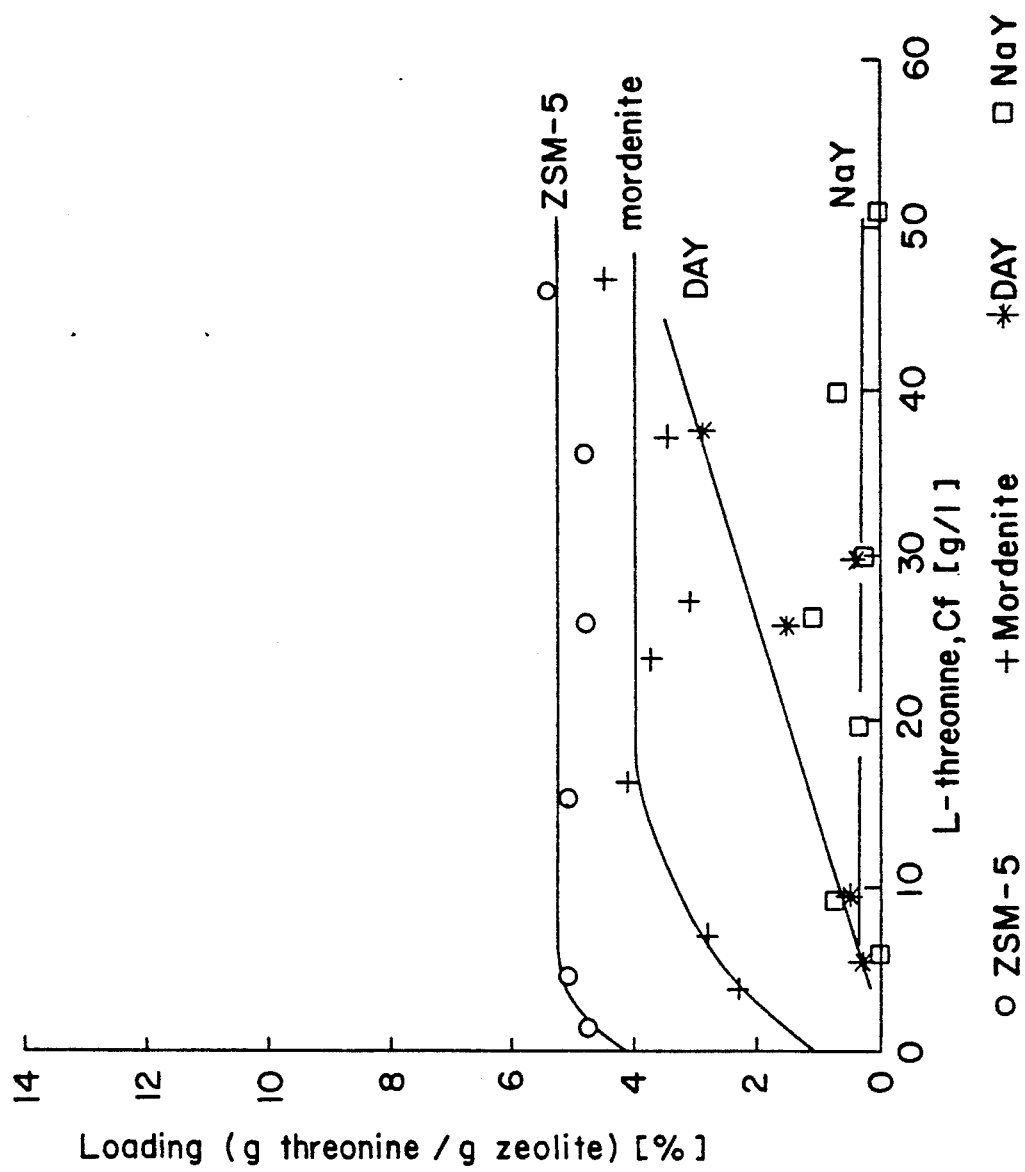
FIG. 3 is a plot of adsorption isotherms of L-threonine on DAY, ZSM-5, mordenite and NaY powders.

Analogous adsorption experiments were carried out with DL-and L-methionine and L-threonine. The results are shown in FIGS. 2 and 3.

2. Working-up of fermentation broths

Figure 4:
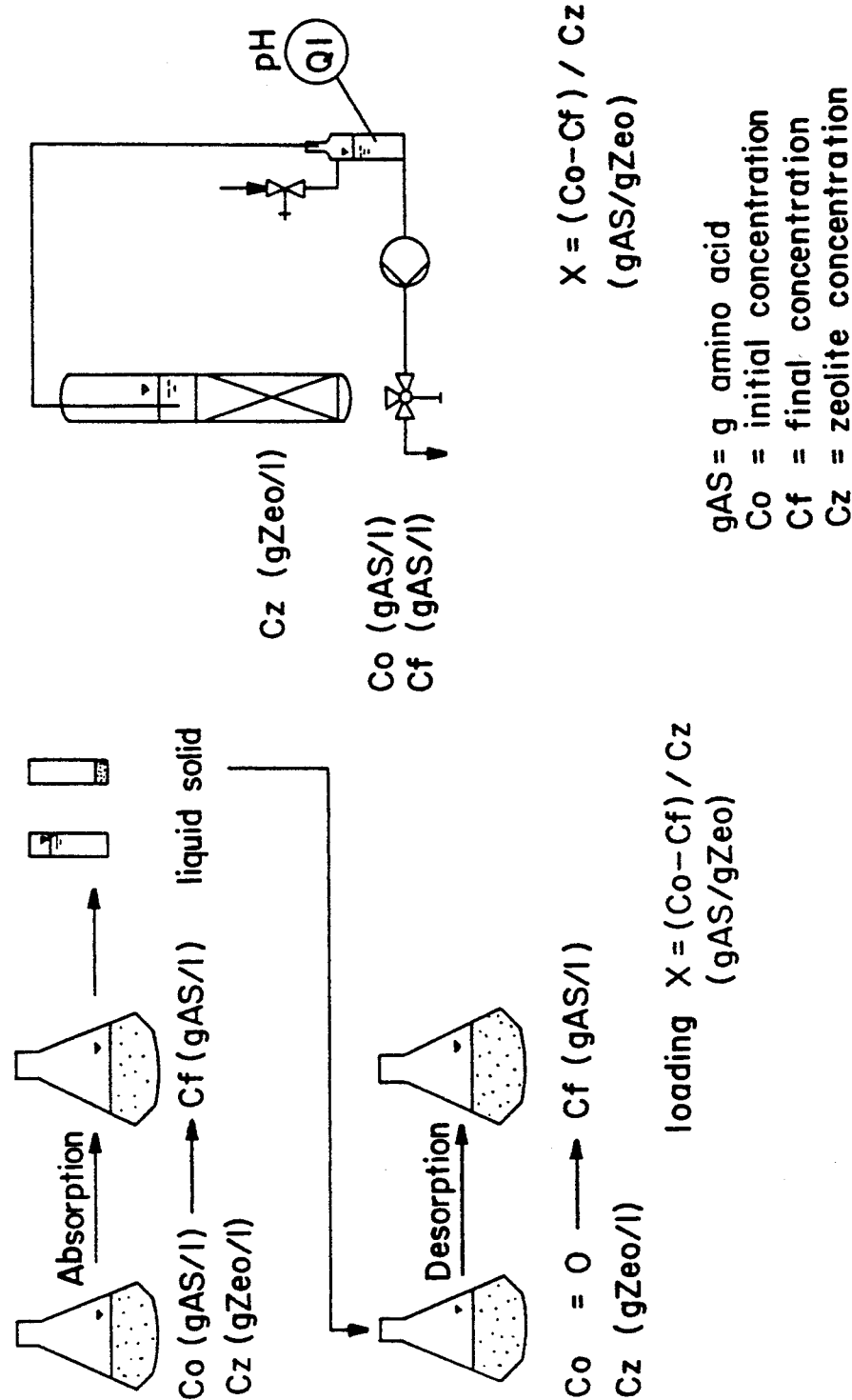
FIG. 4 is a schematic illustration of experiments.

The ad- and desorption properties of L-lysine were also investigated in a fermentation broth. The experiments were carried out in shaker flasks with zeolite powder and in the fixed bed column with molded zeolite bodies at various pH values (FIG. 4).

A sample of about 4 l was withdrawn from a running fermentation, and there were added to it, immediately afterwards, the antibiotic chloramphenicol (0.04 g/l) and the antimycotic pimaricin (0.01 g/l), and the mixture was stored cold. The microbial activity of the production strain was thereby stopped and a foreign infection prevented. Since the adsorption experiments are not carried out under sterile conditions, a contamination could cause the decomposition of lysine and therefore falsify the results of measurements in the course of the experiment.

The medium contains, apart from L-lysine (74 g/l) which has to be separated, several other components, complex constituents, a high salt concentration, a high biomass or protein concentration (dry biomass 30 g/l), microbial by-products and other amino acids. The pH value is near 7.5.

The medium was contacted with the zeolites without separating the biomass and without any pretreatment. In the shaker flask, powdery zeolites were used; and in the fixed-bed column, DAY Raschig rings (external diameter 7 mm × internal diameter 4 mm) and H-ZSM-5 solid cylinders (diameter 3 mm).

The glass fixed-bed columns have an internal diameter of 15 mm and a packed height of 400 mm. The medium was pumped upwards in the column. During this, the pH value in the buffer flask was measured and corrected as required. Ammonia and sulfuric acid were used as correcting agents.

2.1. Results

The pH value in the shaker flask was varied between 7 and 10. The adsorption capacity (loading X) rises with increasing pH value. The maximum loadings of 9 to 12% were reached on the zeolites DAY and NaY.

Ad- and desorption experiments with the fermentation broth are also carried out in the fixed bed column with DAY Raschig rings at pH values between pH 7.5 and 10. At the original pH value (pH 7.5) of the fermentation broth, the adsorption capacity of DAY reaches a loading of ca. 5%. With rising pH value the capacity can be increased to X=12% (at pH 10).

The adsorption capacity of L-lysine in the fermentation broth on DAY, with a maximum of 12%, corresponds to the loading in the synthetically prepared solutions at a pH of about 10, which points to the high selectivity in spite of the many foreign constituents in the broth.

The DAY packing was desorbed with a wash solution (deionized water and hydrochloric acid) at pH 1. The original adsorption loading was 6%. A recovery rate (g of desorbed lysine ÷ g of adsorbed lysine in %) of almost 100% could be reached. The ad- and desorption were repeated several times at different pH values up to 8 cycles in the same column and with the same packing. In the course of this the DAY packing was contacted with the fermentation broth for one week. Neither blockages nor an overgrowth on the column or the Raschig rings were observed.

3. Working-up of fermentation broths in situ

Figure 5:
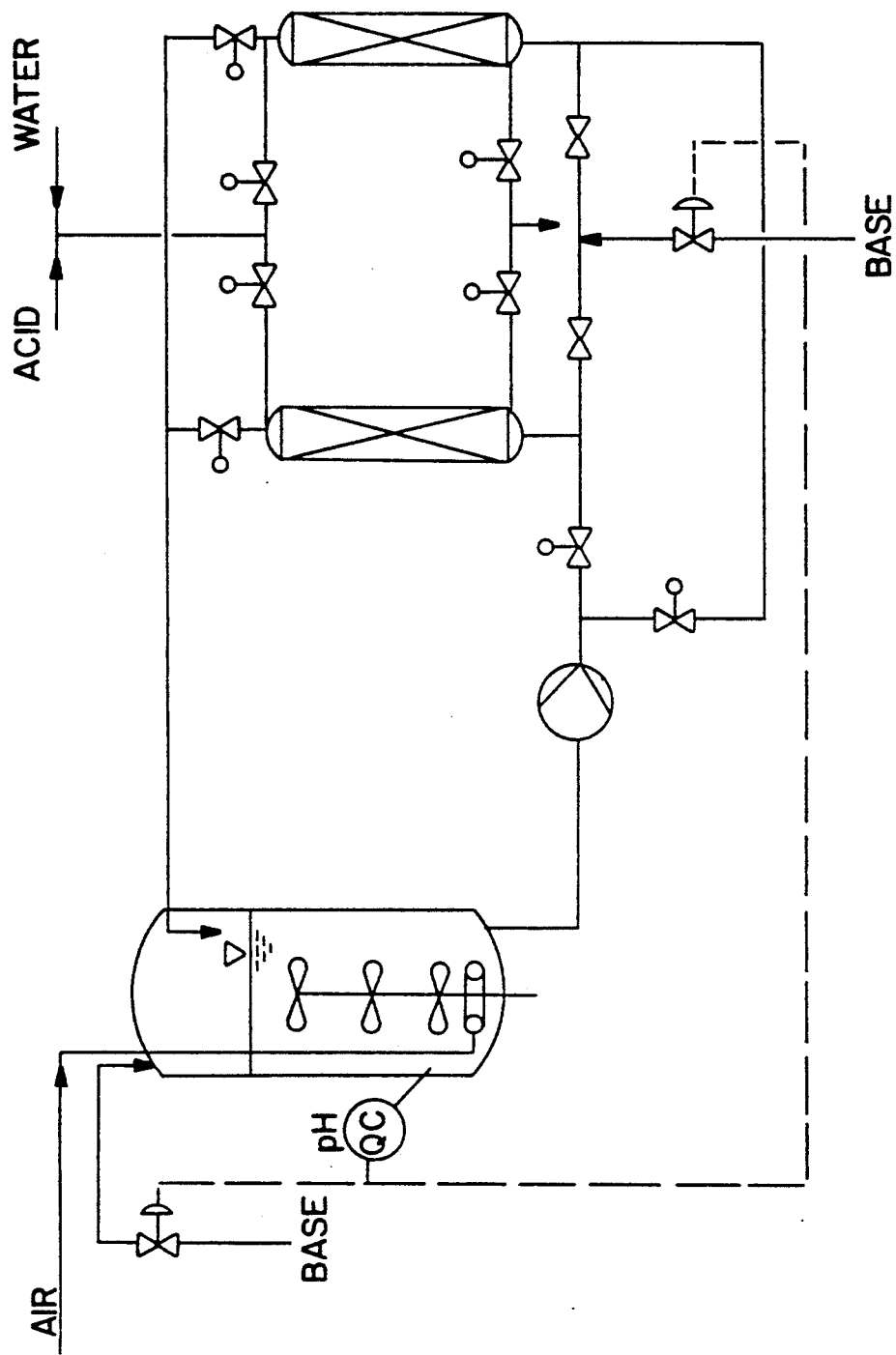
FIG. 5 is a schematic illustration of a apparatus for carrying out the process of the invention.

The results presented up to now admit the possibility of L-lysine being worked up in situ during the fermentation. FIG. 5 shows a diagram of the process. The base ammonia is added to the reactor during the fermentation as a pH correcting agent.

For the in situ workup, fermentation broth is withdrawn from the reactor in the by-pass via a sterile pump. The broth is recycled back to the reactor by pumping via a column with the zeolite packing. No cell separation occurs. L-lysine is adsorbed on the zeolite packing. Low-lysine broth returns to the reactor. The pumping rate or, to be more exact, the residence time in the by-pass and column must be so selected that the cells suffer no damage owing to a shortage of oxygen and substrate.

The correction of the pH value with ammonia could be carried out, instead of at the dosing point on the fermenter, also via the adsorption columns (FIG. 5). As a result of that, temporary pH gradients arise, which drive the adsorption capacity higher. In this connection the residence time of the broth stream in the column as well as the mixing time and the distribution of the pH value over the column must be so optimized that the microorganisms are not damaged.

The column loaded with lysine is then washed with water and eluted with an acid. By the use of hydrochloric acid or sulfuric acid, the corresponding salt, lysine hydrochloride or lysine sulfate, can also be produced. By the use of two columns, the second column can be desorbed during the adsorption in the first. The following values demonstrate the advantages of the process on the production scale.

| | |
|---|---|
| Reactor volume | 300 m³ |
| Working volume | 200 m³ |
| Lysine concentration | 70 g/l |
| Accumulated lysine | 14,000 kg/batch |
| Adsorption capacity of DAY at pH 7.5 | 5% |
| Adsorption capacity of DAY at pH 9.5 | 10% |
| Duration of ad- or desorption | 2 h |
| Two adsorption columns, each | 25 m³ |
| Two adsorption columns, each with | 10,000 kg DAY Raschig rings |
| in-situ workup phase | 40 h |
| Adsorption at pH 7.5, every 2 h | 500 kg lysine |
| At the end of the fermentation | 10,000 kg lysine have been worked up |
| The remaining 4000 kg lysine are separated after the production at pH 9.5 in | 8 h |

According to this example it is possible, 8 hours after the end of the fermentation, to separate lysine completely from the broth and to prepare it for crystallization in the desired form.

What is claimed is:

1. A process for the separation of amino acids from aqueous solutions which comprises adjusting the pH value of a solution of an amino acid, the pH being adjusted to a pH value of $\geq pI$, where pI is the isoelectric point, in the case of basic amino acids (isoelectric point $pI > pH\ 7$), and the pH being adjusted to $pH \leq pI$ in the case of neutral amino acids (pI between 5 and 7) and acidic amino acids ($pI < 5$), then contacting the said solution with a zeolite, and eluting the amino acid adsorbed on the zeolite at a pH value of $pH </pI$ in the case of basic amino acids and $pH > pI$ in the case of neutral and acidic amino acids.

2. A process as set forth in claim 1, in which a zeolites of a type selected from the group consisting of A, X, Y, dealuminized Y zeolite (DAY), mordenite, dealuminized mordenite, ZSM-5, dealuminized ZSM-5, zeolite-$\beta$ and VPI-5 is used.

3. A process as set froth in claim 1 or claim 2 in which L-lysine is separated by use of a zeolite selected from the group consisting of DAY, NaY, ZSM-5 and mordenite.

4. A process as set forth in claim 1 or claim 2 in which DL- or L-methionine is separated by the use of a zeolite selected from the group consisting of ZSM-5, DAY and mordenite.

5. A process as set forth in claim 1 or claim 2 in which L-threonine is separated by use of a zeolite selected from the group consisting of ZSM-5, mordenite and DAY.

6. A process as set forth in claim 1 or claim 2 in which the aqueous solution contains more than one amino acid.

7. A process as set forth in claim 1 or claim 2 in which fermentation broth is withdrawn in a sidestream from a running fermentation and contacted with a suitable zeolite and the liquid depleted in amino acid(s) is returned to the fermentation vessel.

8. A process as set forth in claim 7 in which the biomass is not separated from the fermentation broth.

* * * * *